US009848957B2

(12) United States Patent
Neff et al.

(10) Patent No.: US 9,848,957 B2
(45) Date of Patent: *Dec. 26, 2017

(54) PROTECTIVE WINDOW FOR MEDICAL DEVICE FACEPLATES

(71) Applicant: CERNER INNOVATION, INC., Kansas City, KS (US)

(72) Inventors: Robert A. Neff, Villanova, PA (US); Alan Portnoy, Exton, PA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,543

(22) Filed: Apr. 19, 2017

(65) Prior Publication Data
US 2017/0215987 A1 Aug. 3, 2017

Related U.S. Application Data

(63) Continuation of application No. 14/819,057, filed on Aug. 5, 2015.

(51) Int. Cl.
G06F 17/00 (2006.01)
A61B 90/96 (2016.01)
(Continued)

(52) U.S. Cl.
CPC .............. *A61B 90/96* (2016.02); *A61B 90/98* (2016.02); *G06K 7/1413* (2013.01); *G06K 7/1417* (2013.01)

(58) Field of Classification Search
CPC ...... G06Q 30/02; G06F 7/1008; G07B 15/02; G07B 15/00; G06K 7/10722; G06K 7/14; G06K 17/00; G06K 7/10693
(Continued)

(56) References Cited

U.S. PATENT DOCUMENTS 5,389,711 A 2/1995 Westbrook et al.
5,389,771 A * 2/1995 Amendolia ............ G06K 1/126
235/375

(Continued)

OTHER PUBLICATIONS

Notice of Allowance dated Jan. 20, 2017, in U.S. Appl. No. 14/819,057, 8 pages.
(Continued)

*Primary Examiner* — Karl D Frech
(74) *Attorney, Agent, or Firm* — Shook, Hardy & Bacon L.L.P.

(57) ABSTRACT

Devices are provided that include a protective window integrated with a faceplate for a medical device. In embodiments, a machine-readable identifier adapted to be affixed to an interior portion of a medical device is viewable via a window of a faceplate. Accordingly, the machine-readable identifier is protected from damage during use of the medical device. And, in embodiments, the machine-readable identifier encodes medical-device identifying information to enable tracking the medical device to which it is affixed. As such, should the faceplate require repair or be changed, the machine-readable identifier remains intact and affixed to the medical device. Further embodiments include a device including a faceplate that has a visual signifier of an interiorly placed radio-frequency identifier.

20 Claims, 5 Drawing Sheets

(51) Int. Cl.
*A61B 90/98* (2016.01)
*G06K 7/14* (2006.01)

(58) Field of Classification Search
USPC .......................... 235/375, 380, 454, 462.13
See application file for complete search history.

(56) References Cited

U.S. PATENT DOCUMENTS

| | | |
|---|---|---|
| 5,566,222 A | 10/1996 | Widemann et al. |
| 6,956,572 B2 | 10/2005 | Zaleski |
| 7,278,589 B2 | 10/2007 | Wongosari et al. |
| 7,300,418 B2 | 11/2007 | Zaleski |
| 7,962,544 B2 | 6/2011 | Torok et al. |
| 8,291,337 B2 | 10/2012 | Gannin et al. |
| 8,990,722 B2 | 3/2015 | Gannon et al. |
| 9,218,455 B2 | 12/2015 | Neff |
| 9,501,619 B2 | 11/2016 | Falk et al. |
| 2007/0129983 A1 | 6/2007 | Scherpbier et al. |

OTHER PUBLICATIONS

Non-Final Office Action dated Mar. 24, 2017 in U.S. Appl. No. 15/394,322, 6 pages.
First Action Interview dated Aug. 15, 2016 in U.S. Appl. No. 14/819,057, 5 pages.

\* cited by examiner

PROTECTIVE WINDOW FOR MEDICAL DEVICE FACEPLATES

CROSS-REFERENCE TO RELATED APPLICATIONS

This application is a continuation of U.S. patent application Ser. No. 14/819,057 filed Aug. 5, 2015 and entitled "Protective Window for Medical Device Faceplates" (now U.S. Pat. No. 9,655,687 issued May 23, 2017). U.S. patent application Ser. No. 14/819,057 is hereby incorporated by reference as if set forth in its entirety herein.

BACKGROUND

Barcodes and other machine-readable identifiers are generally used to track the use, maintenance, and movement of medical devices within a hospital or clinical setting. However, barcodes and other machine-readable identifiers are often printed onto adhesive-backed labels that may be affixed to medical devices, as other identification methods and systems may be cost prohibitive. Such labels having printed barcodes are often damaged and/or destroyed during use of the medical device and due to cleaning solvents. As such, a barcode may be obliterated or rendered unreadable due to tearing, ripping, smudging, and peeling-up of label edges, for example. Further, a label including a barcode may be removed from a medical device when a surface of the medical device to which it has been affixed is removed and/or replaced with a new surface (e.g., a replacement part). The removal and loss of the label including a barcode may go unnoticed. In each of the scenarios described, regeneration of the same, unique barcode or creation and entry a completely new, unique barcode is needed, the process of which is time consuming and inconvenient for busy clinicians.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

Embodiments of the present invention relate to a device having a protective window integrated with a faceplate. In embodiments, the device includes a machine-readable identifier adapted to be affixed to an interior surface of a housing of a medical device. The machine-readable identifier encodes medical-device identifying information to enable tracking the medical device corresponding to the housing, in some embodiments. In embodiments, the device further includes a faceplate having an interior surface, an exterior surface, and an opening for housing a window. The faceplate may be configured to be affixed to the housing of the medical device, in embodiments. And the device includes a window. In embodiments, when the faceplate is affixed to the housing, the window overlays at least a portion of the machine-readable identifier such that the at least a portion of the machine-readable identifier is visible at the exterior surface of the faceplate.

Embodiments of the present invention relate to a device having a protective window integrated with a faceplate. In embodiments, the device includes a machine-readable identifier adapted to be affixed to an interior surface of a housing of a medical device, wherein the machine-readable identifier visually encodes medical-device identifying information to enable tracking the medical device corresponding to the housing and to associate the medical device with an electronic medical record. The device includes, in embodiments, a faceplate having an interior surface, an exterior surface, and an opening for housing a window, the faceplate configured to be removeably affixed to the housing of the medical device. In embodiments, the device includes a window. In embodiments, when the faceplate is removeably affixed to the housing, the window overlays at least a portion of the machine-readable identifier such that the at least a portion of the machine-readable identifier is visible at the exterior surface of the faceplate, and encloses the machine-readable identifier between the interior surface of the faceplate and the interior surface of the housing of the medical device.

Embodiments of the present invention relate to a device having a visual signifier to aid in locating an identification tag as integrated with a faceplate for a medical device. In embodiments, the device includes an identifier affixed to an interior surface of a faceplate corresponding to a medical device. The identifier encodes medical-device-identifying information to enable tracking of the medical device, in some embodiments. Additionally or alternatively, the identifier encodes identifying information to enable forming an association of the medical device corresponding to the faceplate with an electronic medical record, in some embodiments. The device further includes a visual signifier positioned on an exterior surface of the faceplate, in embodiments. In some embodiments, the visual signifier is configured to visually communicate the location of the identifier affixed to the interior surface of the faceplate. And in further embodiments, the position of the visual signifier on the exterior surface corresponds to the location of the identifier.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different components, combinations of components, steps, or combinations of steps similar to those described in this document, in conjunction with other present or future technologies.

Embodiments of the present invention are directed toward a window implemented with or integrated into a faceplate of a medical device, such as an infusion pump, for example. The window enables a clinician to clearly view and/or read a machine-readable medical-device identifier, such as a barcode, for example, without needing to remove the faceplate or search to locate the machine-readable medical-device identifier elsewhere on the medical device (e.g., a non-visible surface of the housing of the medical device, or the back exterior surface of the housing of the medical device). In this way, the window protects the machine-readable identifier from spills, scratches, tearing, smudging, and/or peeling (e.g., turned up edges of an adhesive-backed label including said identifier) caused by use, cleaning, and maintenance of the medical device and/or a corresponding faceplate.

Figure 1:
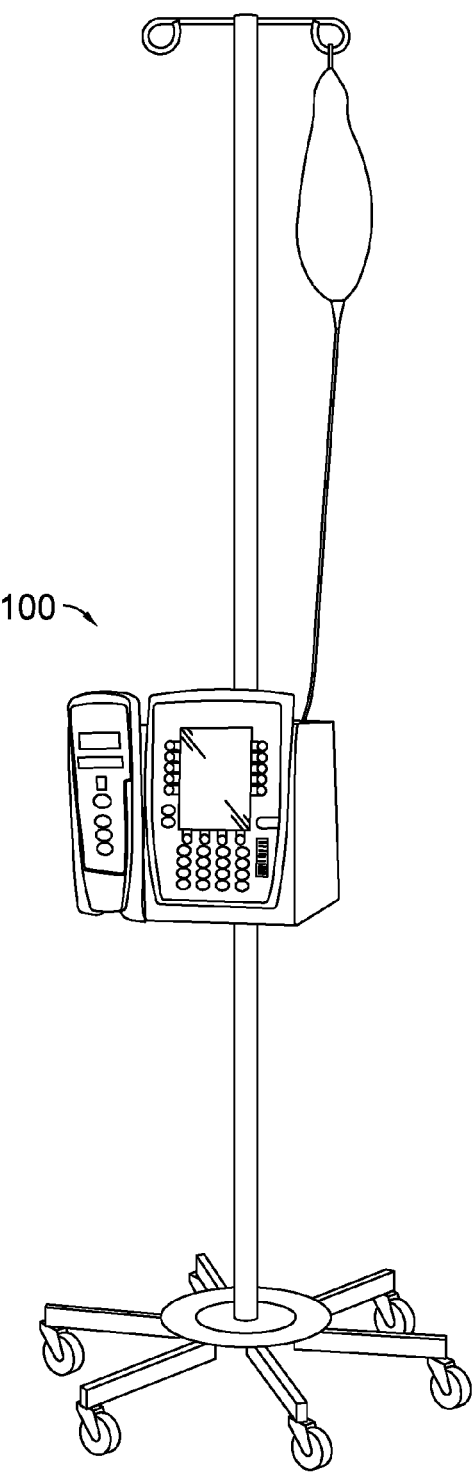
FIG. 1 is an exemplary medical device including a faceplate, in accordance with an embodiment of the invention.

Referring initially to FIG. 1, an exemplary medical device having a faceplate, with which embodiments of the present invention may be implemented, is illustrated and designated generally as reference numeral 100. It will be understood and appreciated by those of ordinary skill in the art that the illustrated medical device 100 is merely an example of one suitable medical device and is not intended to suggest any limitation as to the scope of use or functionality of the invention. Neither should the medical device 100 be interpreted as having any dependency or requirement relating to any single component or combination of components illustrated therein.

Embodiments of the present invention may be operational with numerous other general purpose or special purpose medical devices. The medical device 100 may be any device, stationary or otherwise, that may be used to treat a patient in a clinical setting, such as a hospital, a health care clinic, a doctor's office, a blood drive, etc. For exemplary purposes only and not limitation, medical devices may include fetal heart rate monitors, blood pressure monitors, uterine pressure and contraction activity monitors, blood oxygen saturation monitors, maternal heart rate monitors, other monitors, ventilators, pumps (e.g., balloon pumps), a patient's bed, sequential compression devices, electronic security devices, and the like. In further embodiments, the present invention may be implemented for use with medical devices having highly sensitive patient monitoring capabilities and/or highly accurate treatment-delivery mechanisms. Commonly referred to as "smart" medical devices, such medical devices typically interface with computing hardware and software that may be employed to control, adjust, and tailor performance of one or more functions of said medical devices and any auxiliary components or devices coupled thereto. Accordingly, smart medical devices may generally be connected to a wireless network so as to provide real-time, continuous, and intelligent care delivery, unlike more passive medical devices of the past. Examples of smart medical devices that may be suitable for use with the present invention include, by way of example only, pumps (e.g., infusion), end title carbon dioxide ($EtCO_2$) modules, and other sophisticated and technology-driven devices.

In a clinical setting, the management and treatment of a single patient may command the use of a plurality of medical devices for monitoring physiological responses, delivering therapeutic agents (e.g., pharmaceuticals, fluids), and the like. In order to deliver superior health care to patients, a large number and variety of medical devices may be utilized and employed. In addition to manual maintenance (e.g., on moving parts) performed on medical devices, smart medical devices in particular may utilize software and/or hardware-based maintenance, such as the download of a firmware update, for example.

Figure 2:
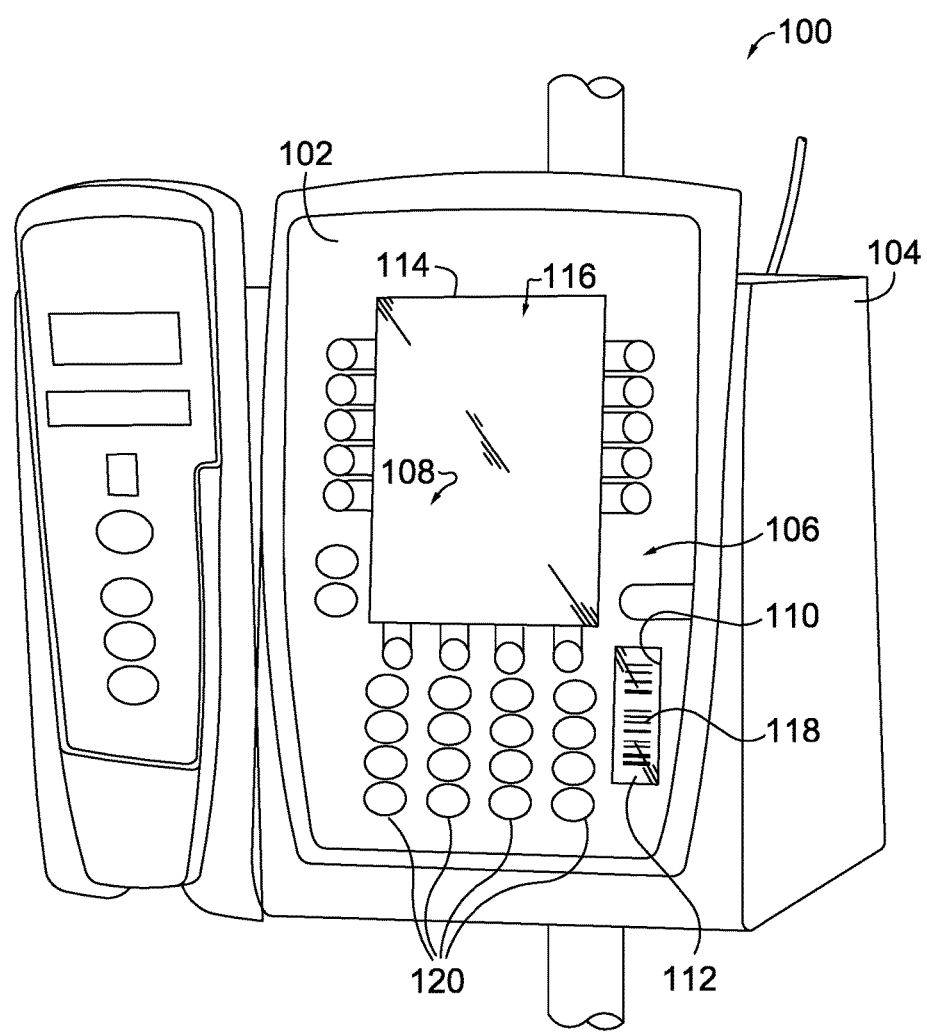
FIG. 2 is a right perspective detail view of the exemplary medical device including the faceplate shown in FIG. 1, in accordance with an embodiment of the invention.

Turning to FIG. 2, it depicts a right perspective view of the exemplary medical device 100 including the faceplate 102 shown in FIG. 1, in accordance with an embodiment of the present invention. The faceplate 102 is a component that generally provides a user interface (e.g., buttons, knobs) for interacting with the medical device 100. Accordingly, the faceplate 102 is configured to be affixed to the housing 104 of the medical device 100. In some embodiments, the faceplate 102 is adapted to be removeably affixed to the medical device 100 (e.g., housing 104) such that the faceplate 102 may stay securely in place during use and transport of the medical device 100, but such that the faceplate 102 may also be removed should the faceplate 102 need to be replaced and/or repaired. In general, the faceplate is removeably affixed, meaning that the faceplate is configured to be affixed to the medical device 100 and configured to be removed from the medical device 100 without damaging the faceplate, for example. The faceplate 102 includes an interior surface (not shown) and an exterior surface 106. The exterior surface 106 may be outward and/or upward facing with respect to the internal components of a medical device 100, and as such, a clinician may easily access and view the exterior surface 106 of the faceplate 102 when a clinician is in a standing position at the bedside of a patient, for example. The faceplate 102 serves to provide information to a clinician and enable the clinician to control, program, and/or otherwise operate the medical device using buttons, knobs, dials, and the like. The faceplate 102 may protect a graphical user interface (GUI) 108 such as a touchscreen display. A GUI may include a monitor, computer screen, project device, or other hardware device for displaying output capable of displaying graphical user interfaces. The faceplate 102 provides a clean, aesthetically pleasing appearance while covering at least a portion of the medical device 100, including internal components and/or a GUI 108, in some embodiments. The faceplate 102 may further protect the medical device and components therein from spills, splashes, cleaning solvents, scratches, and impacts.

In embodiments, the faceplate 102 includes an opening 110 for housing a window 112. The opening 110 is adapted to receive at least a portion of a window 112, in embodiments. The opening 110 may further be adapted to securely retain at least a portion of a window 112 inserted or positioned therein. Generally, the opening 110 may be similar or the same in size and shape as a window 112 adapted for said opening 110. In further embodiments, the position and dimensions of a first opening 110 correspond to the position and dimensions of a first window (e.g., 112) and the machine-readable identifier 118, while the position and dimensions of a second opening (e.g., opening 114) correspond to the position and dimensions of a second window (e.g., window 116) further corresponding to the GUI 108 of a medical device 100.

In embodiments, window 112 is adapted to be secured to the faceplate 102 so as to span opening 110 completely or at least partially. In some embodiments, window 112 is adapted to be integrated into opening 110. The window 112 is at least semi-transparent, in embodiments. In some embodiments, the window 112 comprises one or more materials that are semi-transparent or transparent. The window 112 provides visibility via the opening 110 of the faceplate 102 from the exterior surface 106 of the faceplate 102. As such, the window 112 may be positioned so that a machine-readable identifier 118 is visible when the faceplate 102, as affixed to the exemplary medical device 100, is viewed from the exterior surface 106 of the faceplate 102.

In some embodiments, the medical device 100 may need refurbishment or replacement of parts, such as the faceplate 102 that fits onto the housing 104 of the medical device 100. The faceplate 102 may include a plurality of objects 120 for user interaction. In embodiments, the faceplate 102 may include one or more of the following objects for controlling, programming, and adjusting configurations and functions of the medical device: a GUI (e.g., 108), I/O components, physical buttons, virtual buttons, switches, dials, knobs, a keyboard, and the like, for example. The plurality of objects 120 may be manipulated by a user, such as a clinician, in order to use the medical device 100 to provide health care services to a patient. Over time, one or more of the plurality of objects 120 may wear out from use, such that at least one of the objects 120 may be unresponsive when depressed, may necessitate the use of extra force to elicit the desired response (e.g., selection of an option indicated on the GUI 108, increasing an amount to be dispensed by a medical device, setting a flow rate), or may necessitate the use several depressions to register a single depression that elicits a response. This makes interaction with the medical device 100 an inconvenience and an annoyance for clinicians. At such a time, any worn-out, malfunctioning, and/or poorly operating objects of the faceplate 102 may be replaced to restore fully functioning interactive objects to the medical device 100.

A machine-readable identifier 118, such as a barcode for example, may be visible at the faceplate 102, in some embodiments. Exemplary machine-readable identifiers include a one-dimensional barcode (e.g., a Codabar), a two-dimensional barcode (e.g., a quick response (QR) code), and the like. The machine-readable identifier 118 may encode medical-device specific information, such as an identifier that is unique to a single medical device such that the medical device may be differentiated from other same or similar medical devices.

The machine-readable identifier 118 may be used to enable tracking of a particular medical device, including the use, function, repair, and storage of said medical device, in a clinical setting, for example. The machine-readable identifier 118 may be utilized in any number of useful ways. For instance, using a machine, such as a barcode scanner, for example, the machine-readable identifier 118 may be scanned and information encoded therein or linked to therein may be "read" by a barcode scanner for example, or processed to locate information corresponding to the machine-readable identifier 118.

Exemplary machines for reading the machine-readable identifier 118 may include a barcode scanner, a camera, a sensor, and other devices having I/O components and software for processing the information stored in, associated with, or linked to the machine-readable identifier 118. The medical device 100 and faceplate 102 corresponding to the machine-readable identifier 118 may be associated with other information accessed, selected, scanned, or otherwise read immediately prior to or immediately after the machine-readable identifier 118 has been read, in some embodiments. For example, a patient-identifying wristlet may be scanned, followed by a scan of an intravenous (IV) fluid to be administered to the patient, and further followed by a scan of the machine-readable identifier 118 of the medical device 100, which is to be used to administer the scanned IV fluid to the patient having the scanned wristlet. In such an embodiment, detailed and identifying information for each of the medical device 100, the IV fluid, and the patient may be electronically linked in an electronic medical record (EMR), for example. The machine-readable identifier 118 may, in some embodiments, enable the particular medical device 100 corresponding to the scanned machine-readable identifier 118 to become associated with an identified patient, an EMR corresponding to the particular identified patient, and/or with a particular instance of administration of a therapeutic agent, for example.

As utilized herein, the acronym "EMR" is not meant to be limiting, and may broadly refer to any or all aspects of the patient's medical record rendered in a digital format. Generally, the EMR is supported by systems configured to coordinate the storage and retrieval of individual records with the aid of computing devices. As such, a variety of types of health care related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of health care.

In embodiments, upon reading the machine-readable identifier 118, the medical device 100 and faceplate 102 corresponding therewith may become associated with a maintenance order, for example, a work order to replace the faceplate 102, swap the faceplate 102, purchase a new faceplate, or other action regarding the medical device 100 and/or faceplate 102. In another embodiment, the machine-readable identifier 118 may be read to electronically record the status of a maintenance order, for example, to document a time, date, and/or location corresponding to when repair work is initiated, is in progress, is delayed for a part shipment, and/or has been completed. In yet another embodiment, upon reading a machine-readable identifier 118, the medical device 100 and faceplate 102 corresponding therewith may be counted as part of an inventory check, such as placement of the medical device 100 into storage (e.g., when the medical device 100 is not to be used) or removing the medical device 100 from storage (e.g., when the medical device 100 is planned to be used).

Due to the position of the machine-readable identifier 118 on the faceplate 102, said machine-readable identifier 118 may be lost due to faceplate 102 replacement, removed accidently by peeling, or otherwise obliterated by cleaning solvents and other wear and tear. To circumvent this, the machine-readable identifier 118 may be placed elsewhere on the medical device 100 in other embodiments. However, this makes locating the machine-readable identifier 118 difficult for a clinician, and further may make reading the machine-readable identifier 118 unwieldy, depending on the final placement of the machine-readable identifier 118 on a surface of the medical device 100.

As depicted in FIG. 2, a machine-readable identifier 118 is visible at the exterior surface 106 of the faceplate 102. The machine-readable identifier 118 may be adapted to be affixed to an interior surface of a housing 104 of a medical device 100. For example, the machine-readable identifier 118 may be included on an adhesive-backed label that may be affixed to an interior surface of the housing 104 of the medical device 100. As referred to herein, an interior surface of the medical device housing refers to a surface of the medical device 100 that may be, at least, partially covered or contacted by the faceplate 102 affixed thereon in embodiments. In some embodiments, the interior surface of the medical device housing 104 is a surface of the housing 104 that is adapted to contact and/or receive at least a portion of an interior surface (not shown in FIG. 2) of the faceplate 102 and/or attachment means thereon. Accordingly, the machine-readable identifier 118 may be positioned at or on the interior surface of the housing 104 such that the position and at least one dimension (e.g., size, width, shape) of the machine-readable identifier 118 may be similar to the position and at least one dimension of the window 112 that may be housed in the opening 110 of the faceplate 102. For example, the length of a machine-readable identifier 118 may be the same as or similar to the length of the opening 110 and/or the window 112. In another example, the length and width of the machine-readable identifier 118 may be the same as or similar to the length and width of the opening 110 and/or the window 112. In such exemplary embodiments, one or more dimensions and/or a position of the machine-readable identifier 118 may, at least, partially align with one or more dimensions and/or a position of the window 112 when the faceplate 102 is affixed to the housing 104. As such, when the faceplate 102 may be affixed to the housing 104, the machine-readable identifier 118 appears to be aligned with the window 112 such that a clinician has a clear line-of-sight of the machine-readable identifier 118 from the exterior surface 106 of the faceplate 102.

Figure 3:
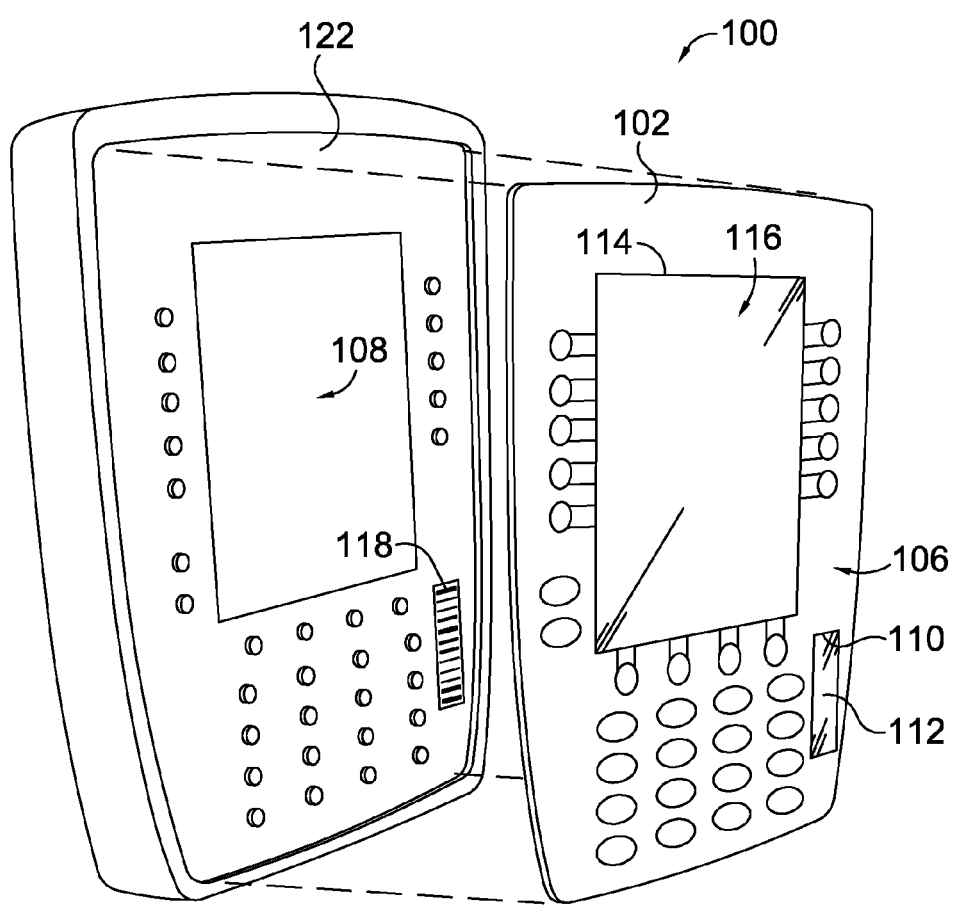
FIG. 3 is an exploded perspective view of the exemplary medical device including the faceplate shown in FIG. 1, in accordance with an embodiment of the invention.

Turning now to FIG. 3, it depicts an exploded view of the exemplary medical device 100 including a faceplate 102 shown in FIG. 1, in accordance with an embodiment of the present invention. As illustrated in FIG. 3, the position of the machine-readable identifier 118 and the position of the window 112 may at least partially align with one another. In further embodiments, at least one window (e.g., window 112) overlays at least a portion of the machine-readable identifier 118 so that the at least a portion of the machine-readable identifier 118 is visible at the exterior surface 106 of the faceplate 102. Additionally, the window 112 shown as positioned in opening 110 provides protection to the machine-readable identifier 118, such that the machine-readable identifier 118 may be enclosed between the interior surface of the faceplate 102 and the interior surface 122 of the housing 104 of the medical device 100. Similarly, a second window (e.g., window 116) shown positioned in second opening 114 provides protection to the GUI 108 of a medical device 100.

Although the faceplate 102 depicted in FIG. 3 appears to fit snugly into the housing 104 of the medical device 100, it will be understood by those in the art that other configurations are considered to be within the scope of the invention. For example, the faceplate 102 may fit onto the housing 104, rather than into the housing 104. In another example, the faceplate 102 may fit over the housing 104. Any number of variations for attaching the faceplate 102 to the housing 102 is considered to be within the scope of the invention.

Figure 4:
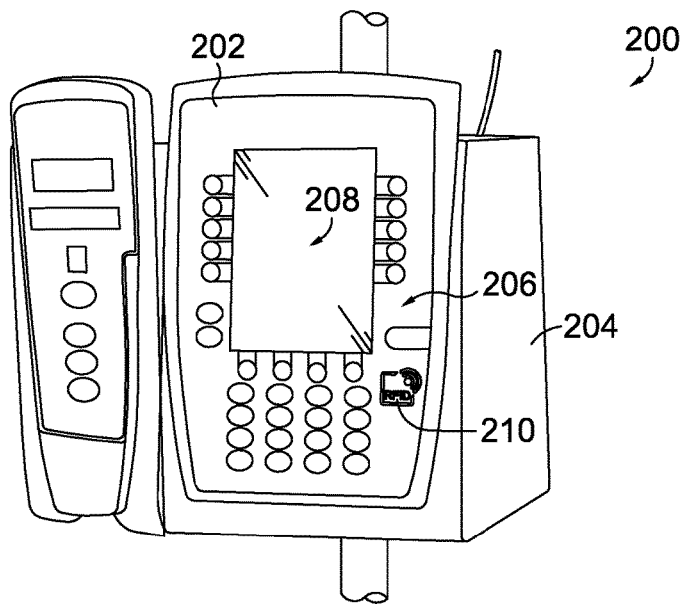
FIG. 4 is a plan view of an exterior surface of an exemplary faceplate for a medical device, in accordance with an embodiment of the invention.

Referring to FIG. 4, it illustrates a perspective view of faceplate 202 for an exemplary medical device 200. The faceplate 202 is coupled to a housing 204 of the medical device 200, as shown in the embodiment of FIG. 4. The faceplate 202 includes an exterior surface 206. The exterior surface 206, generally, is outward and/or upward facing with respect to internal components of the medical device 200, and as such, a clinician may easily access and view the exterior surface 206 of the faceplate 202 when a clinician is in a standing position at the bedside of a patient, for example. The faceplate 202 serves to provide information to a clinician and enable the clinician to control, program, and/or otherwise operate the medical device 200 using buttons, knobs, dials, and the like. The faceplate 202 may protect a GUI 208, such as a touchscreen display, for example.

The exterior surface 206 further includes a visual signifier 210. The visual signifier 210 is configured to visually communicate the location of an identifier affixed to an interior surface of the faceplate 202. In some embodiments, the identifier is an RFID-emitting device (e.g., a tag or a chip) that may be affixed to an interior surface of the faceplate 202. In another embodiment, the identifier is adapted for use in a real-time locating system (RTLS), wherein real-time as used herein may include latency inherent to computing systems. As used herein, visually communicate refers to the capability to communicate a message to a user, such as a clinician for example, visually. A visual signifier 210, as used herein, refers to text, a symbol, an icon, a graphic, or combination thereof that may be associated with a message or function. For example, an exclamation point centered within a triangular shape is a symbol that may be recognized by a user as communicating "caution."

In another example, a small circle having three concentric circle segments radiating upward the outward from the small circle and graduating in size may be recognized by a user as communicating Wi-Fi functionality. The visual signifier 210 may also include color to communicate a desired message or functionality. For example, a red-colored letter "X" may be recognized to communicate a cancellation function or a stop function. The size of the visual signifier 210 may be used to communicate information as well. For instance, the visual signifier 210 may have a size and dimensions that are the same as or similar to the size and dimensions (e.g., a "footprint") of an RFID device, such that the visual signifier 210 indicates an area where an RFID-reading device may be placed at or near the exterior surface 206 for reading the RFID device at or near the interior surface. In another embodiment, the visual signifier 210 may not similar in size and/or dimension (e.g., a "footprint") of a device (e.g., a tag) adapted for user in a real-time location system (RTLS), such that the visual signifier 210 indicates that said device is associated with the faceplate 202. In another example, a device (e.g., tag adapted for use in a RTLS) may be found without requiring a locating device to be placed at or near the exterior surface 206, for example.

In another example, the visual signifier 210 may incorporate a light, such as an LED for example, as part of the visual signifier 210 in order to draw a user's eye to the area of the visual signifier 210 as positioned on the exterior surface 206 of the faceplate 202. In embodiments, the position of the visual signifier 210 on or at the exterior surface 206 of the faceplate 202 corresponds to a location of the RFID device. As such, a clinician may position an RFID-reading device close to or near the visual signifier 210 in order to read an RFID device located therein. In some embodiments, a passive RFID device requires an RFID-reading device to be within a defined distance or proximity to the RFID device in order to trigger an emission of an RFID from the RFID device.

Figure 5:
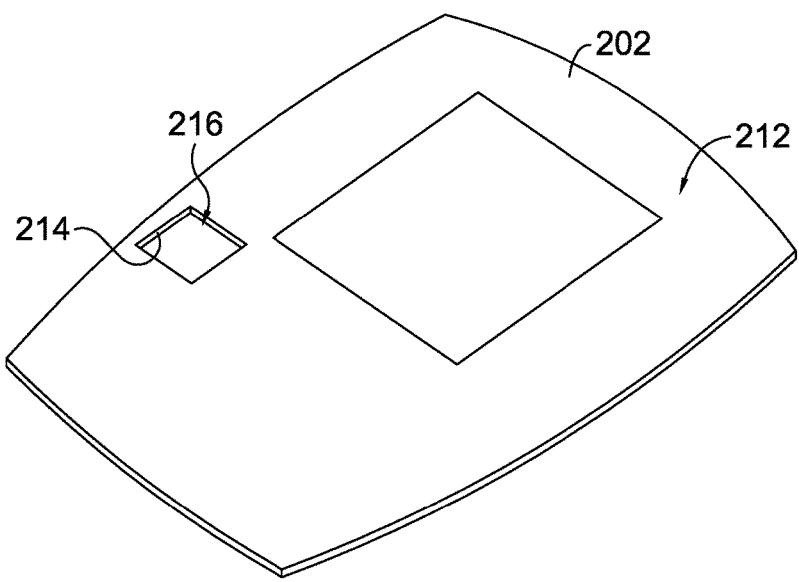
FIG. 5 is a plan view of an interior surface of the exemplary faceplate of FIG. 4, in accordance with an embodiment of the invention.

Referring to FIG. 5, it illustrates a perspective view of the exemplary faceplate 202 of FIG. 4, in accordance with an embodiment of the present invention. As illustrated, the faceplate 202 includes an interior surface 212. The interior surface 212 of the faceplate 202 includes at least one portion 214 adapted to receive a device for tracking, such as a "tag" or chip adapted for use with RFID systems or RTLS (not shown). The interior surface 212 of the faceplate 202 may include one or more edges 216 that form a perimeter of the at least one portion 214 of the interior surface 212. In some embodiments, the at least one portion 214 is recessed. As such, the device for tracking may be inserted into said recess created by the portion 214. The one or more edges 216 may aid in securing a device for tracking therein. In embodiments, the interior surface of the faceplate includes attachment means for receiving the device for tracking and retaining the device for tracking therein.

Figure 6:
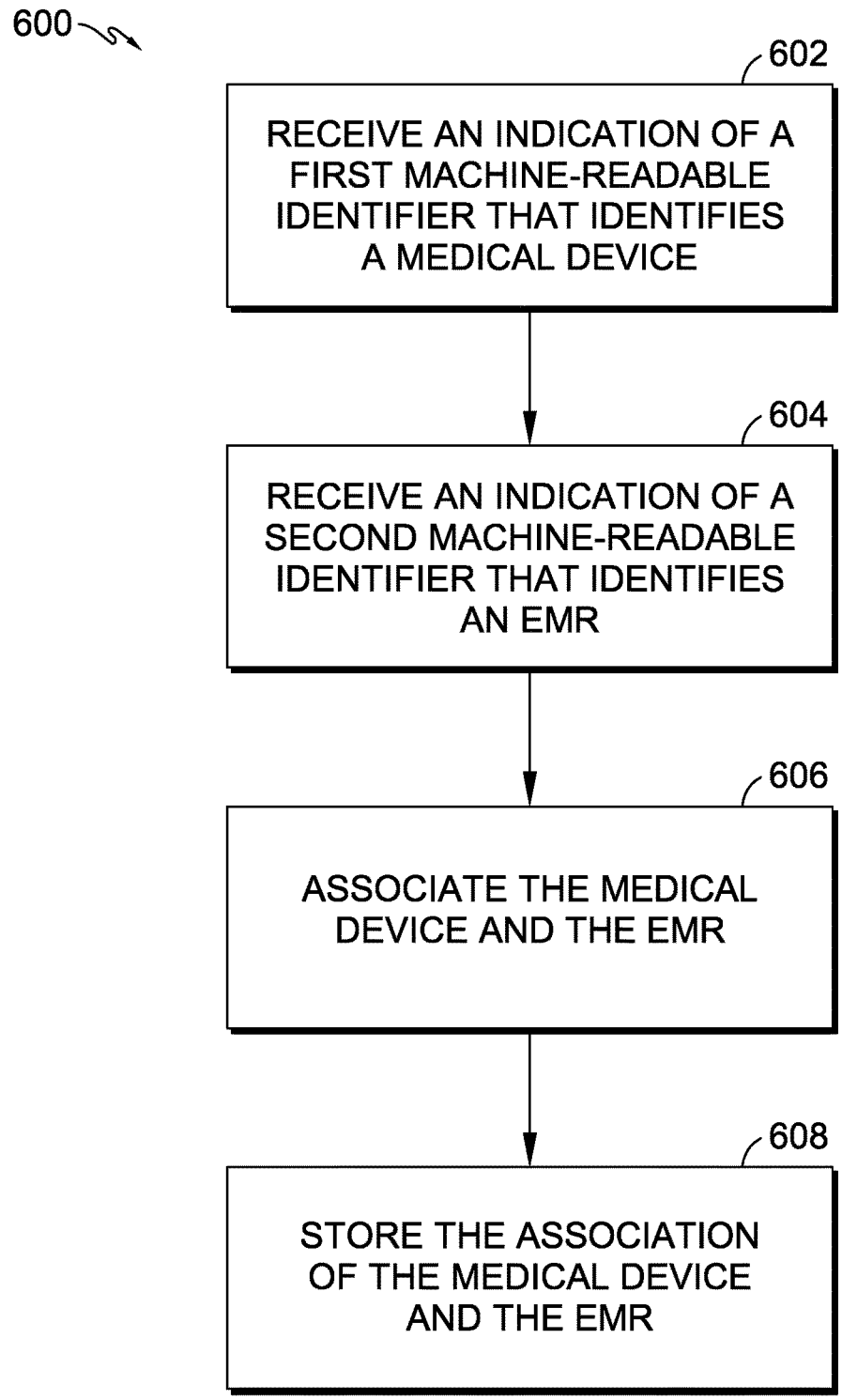
FIG. 6 is an illustrative flow diagram of an exemplary method for utilizing a machine-readable identifier, in accordance with an embodiment of the invention.

Turning to FIG. 6, it illustrates a flow chart of an exemplary method 600 for utilizing a machine-readable identifier, in accordance with an embodiment of the present invention. At block 602, the method 600 includes receiving an indication of a first machine-readable identifier. In some embodiments, the first machine-readable identifier may be affixed to an interior surface of a housing of a medical device. The first machine-readable identifier may be affixed to an interior surface of a faceplate, in other embodiments. Generally, the first machine-readable identifier is usable to identify and distinguish the medical device from other medical devices. In one embodiment, the first machine-readable identifier is a barcode visible through a window of a faceplate of a medical device. In some embodiments, the first machine-readable identifier that includes a barcode is read using a scanning device.

In another embodiment, the first machine-readable identifier is a RFID that is not visible at the exterior surface of a faceplate of a medical device. In some embodiments, the first machine-readable identifier that includes an RFID (e.g., a near field communication identifier tag) is read by a capable device. An RFID may be passive or active, such that a passive RFID is not coupled to a power source (e.g., passive RFID may be powered by an electromagnetic field generated by the RFID reader), whereas an active RFID is coupled to a power source (e.g., a battery). In further embodiments, the first machine-readable identifier includes one or more of a barcode and an RFID, such that a scanning device and or an RFID-reading device may be used to identify the medical device.

In another embodiment, the first machine-readable identifier is a tag adapted for use in an RTLS that is not visible at the exterior surface of a faceplate of a medical device. In some embodiments, the first machine-readable identifier that includes a tag adapted for use in an RTLS is read or located by a capable device. In further embodiments, the first machine-readable identifier includes one or more of a barcode and a tag adapted for use in an RTLS, such that a locating device and or reading device may be used to identify the medical device At block 604, the method 600 includes receiving an indication of a second machine-readable identifier that is not the same as the first machine-readable identifier, wherein the second machine-readable identifier is usable to identify an electronic medical record of a patient. Next, the medical device and the EMR of the patient are associated with one another, shown at block 606. The first machine-readable identifier corresponding to the medical device may be associated with and/or linked to the second machine-readable identifier corresponding to the patient. Then at block 608, the association of the medical device and the EMR is stored. The association of the medical device and the EMR may be stored in a local database, a centralized database, or both, for redundancy. Similarly, in embodiments, an association of a first machine-readable identifier corresponding to the medical device and a second machine-readable identifier corresponding to the EMR may be stored. It will be understood by those in the art that the method 600 may be practiced utilizing exemplary device 200, for example.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A device having a protective window integrated with a faceplate, the device comprising:
   a machine-readable identifier adapted to be affixed to an interior surface of a housing of a medical device, wherein the machine-readable identifier encodes medical-device identifying information to enable tracking the medical device corresponding to the housing; and
   a faceplate having an interior surface, an exterior surface, and an opening for housing a window, the faceplate configured to be affixed to the housing of the medical device.

2. The device of claim 1, wherein a position and at least one dimension of the opening corresponds to a position and at least one dimension of the machine-readable identifier when the faceplate is affixed to the housing.

3. The device of claim 1, wherein at least one dimension of the faceplate corresponds to at least one dimension of the housing.

4. The device of claim 1, wherein the faceplate is further configured to enclose at least a quarter of the interior surface of the housing of the medical device when the faceplate is affixed to the housing.

5. The device of claim 1, further comprising a window, wherein when the faceplate is affixed to the housing, and wherein the window overlays at least a portion of the machine-readable identifier such that the at least a portion of the machine-readable identifier is visible at the exterior surface of the faceplate.

6. The device of claim 5, wherein a position and at least one dimension of the opening corresponds to a position and at least one dimension of the window.

7. The device of claim 5, wherein the window comprises one or more materials that are at least semi-transparent.

8. The device of claim 1, wherein the machine-readable identifier further encodes operating specifications of the medical device.

9. The device of claim 1, wherein the machine-readable identifier includes one or more of a one-dimensional barcode and a two-dimensional barcode.

10. The device of claim 1, wherein the machine-readable identifier further encodes clinical facility identifying information to enable tracking the medical device corresponding to the housing.

11. A device having a protective window integrated with a faceplate, the device comprising:
    a machine-readable identifier adapted to be affixed to an interior surface of a housing of a medical device, wherein the machine-readable identifier visually encodes medical-device identifying information to enable tracking the medical device corresponding to the housing and to associate the medical device with an electronic medical record; and a faceplate having an interior surface, an exterior surface, and an opening for housing a window, the faceplate configured to be removeably affixed to the housing of the medical device.

12. The device of claim 11, wherein the machine-readable identifier includes one or more of a one-dimensional barcode and a two-dimensional barcode.

13. The device of claim 11, wherein the machine-readable identifier further encodes clinical facility identifying information to enable tracking the medical device corresponding to the housing.

14. The device of claim 11, wherein a position and at least one dimension of the opening corresponds to a position and at least one dimension of the machine-readable identifier when the faceplate is removeably affixed to the housing.

15. The device of claim 11, wherein the housing is configured to receive and retain the faceplate thereby facilitating affixing the faceplate to the housing.

16. The device of claim 11, further comprising a window, wherein when the faceplate is removeably affixed to the housing, the window:

overlays at least a portion of the machine-readable identifier such that the at least a portion of the machine-readable identifier is visible at the exterior surface of the faceplate, and encloses the machine-readable identifier between the interior surface of the faceplate and the interior surface of the housing of the medical device.

17. The device of claim 16, wherein a position and at least one dimension of the opening corresponds to a position and at least one dimension of the window.

18. The device of claim 16, wherein the window comprises one or more materials that are at least semi-transparent.

19. A device having a visual signifier to aid in locating an identification tag as integrated with a faceplate for a medical device, the device comprising:

an identifier affixed to an interior surface of a faceplate corresponding to a medical device, wherein the identifier encodes identifying information to enable tracking of the medical device and the forming of an association between the medical device and an electronic medical record;

a visual signifier positioned on an exterior surface of the faceplate, the visual signifier configured to visually communicate the location of the identifier affixed to the interior surface of the faceplate, wherein the position of the visual signifier on the exterior surface of the faceplate corresponds to the location of the identifier affixed to the interior surface of the faceplate such that the visual signifier visually communicates a location where a user may position a reading device in order to read the identifier.

20. The device of claim 19, wherein the device further includes a battery configured to power the identifier, and wherein the identifier is adapted for use in a real-time location system (RTLS).

* * * * *